United States Patent [19]
Christy

[11] Patent Number: 5,613,975
[45] Date of Patent: *Mar. 25, 1997

[54] ENDOSCOPIC SUTURING DEVICE AND METHOD

[76] Inventor: William J. Christy, 1324 Sunset Dr., Winter Park, Fla. 32789

[ * ] Notice: The term of this patent shall not extend beyond the expiration date of Pat. No. 5,503,634.

[21] Appl. No.: 438,021

[22] Filed: May 8, 1995

Related U.S. Application Data

[63] Continuation-in-part of Ser. No. 127,775, Sep. 27, 1993, Pat. No. 5,503,634, which is a continuation-in-part of Ser. No. 54,856, Apr. 28, 1993, Pat. No. 5,350,385.

[51] Int. Cl.⁶ .................................................. A61B 17/00
[52] U.S. Cl. ........................ 606/144; 606/139; 112/169; 223/102
[58] Field of Search ..................................... 606/139, 144, 606/145, 146, 147, 148; 112/169, 80.03, 80.06; 223/102–104; 206/380

[56] References Cited

U.S. PATENT DOCUMENTS

| | | |
|---|---|---|
| 373,372 | 11/1887 | La Forest King . |
| 389,235 | 9/1888 | McBrayer . |
| 2,072,209 | 3/1937 | Jones ........................ 223/102 |
| 2,327,353 | 12/1940 | Karle . |
| 3,638,653 | 2/1972 | Berry . |
| 3,840,017 | 10/1974 | Violante . |
| 4,011,873 | 3/1977 | Hoffmeister . |
| 5,152,769 | 10/1992 | Baber . |
| 5,211,650 | 5/1993 | Noda ........................ 606/139 |
| 5,312,360 | 5/1994 | Behl ........................ 604/106 |
| 5,336,239 | 8/1994 | Gimpelson ............... 606/223 |
| 5,364,408 | 11/1994 | Gordon . |
| 5,368,601 | 11/1994 | Sauer et al. . |
| 5,397,325 | 3/1995 | Della Badia et al. . |
| 5,403,328 | 4/1995 | Shallman ............... 112/80.03 |
| 5,439,469 | 8/1995 | Heaven et al. ......... 606/144 |

FOREIGN PATENT DOCUMENTS

| | | | |
|---|---|---|---|
| 1093329 | 5/1984 | U.S.S.R. | ............... 606/145 |

*Primary Examiner*—Jeffrey A. Schmidt
*Attorney, Agent, or Firm*—Allen, Dyer, Doppelt, Milbrath & Gilchrist, P.A.

[57] ABSTRACT

A surgical suturing apparatus for closing an incision penetrating a plurality of layers of tissue includes a tubular body in which a "J"-shaped suture needle resides. In this position the tubular body may be inserted into the incision without damaging tissue. Once the tubular body has been inserted into the incision, the pointed end and suture gate of the suture needle are deployable out of a slot through the side of the tubular body to permit deep suturing of tissue layers without also suturing surface tissue layers. Several embodiments are presented for deploying the needle, including one in which the straight section of the suture needle having the pointed tip is biased to flare away from the other straight section of the suture needle, and the deploying is accomplished by moving the pointed tip section adjacent the tubular body slot and permitting the bias to cause that section to flare out of the slot.

25 Claims, 11 Drawing Sheets

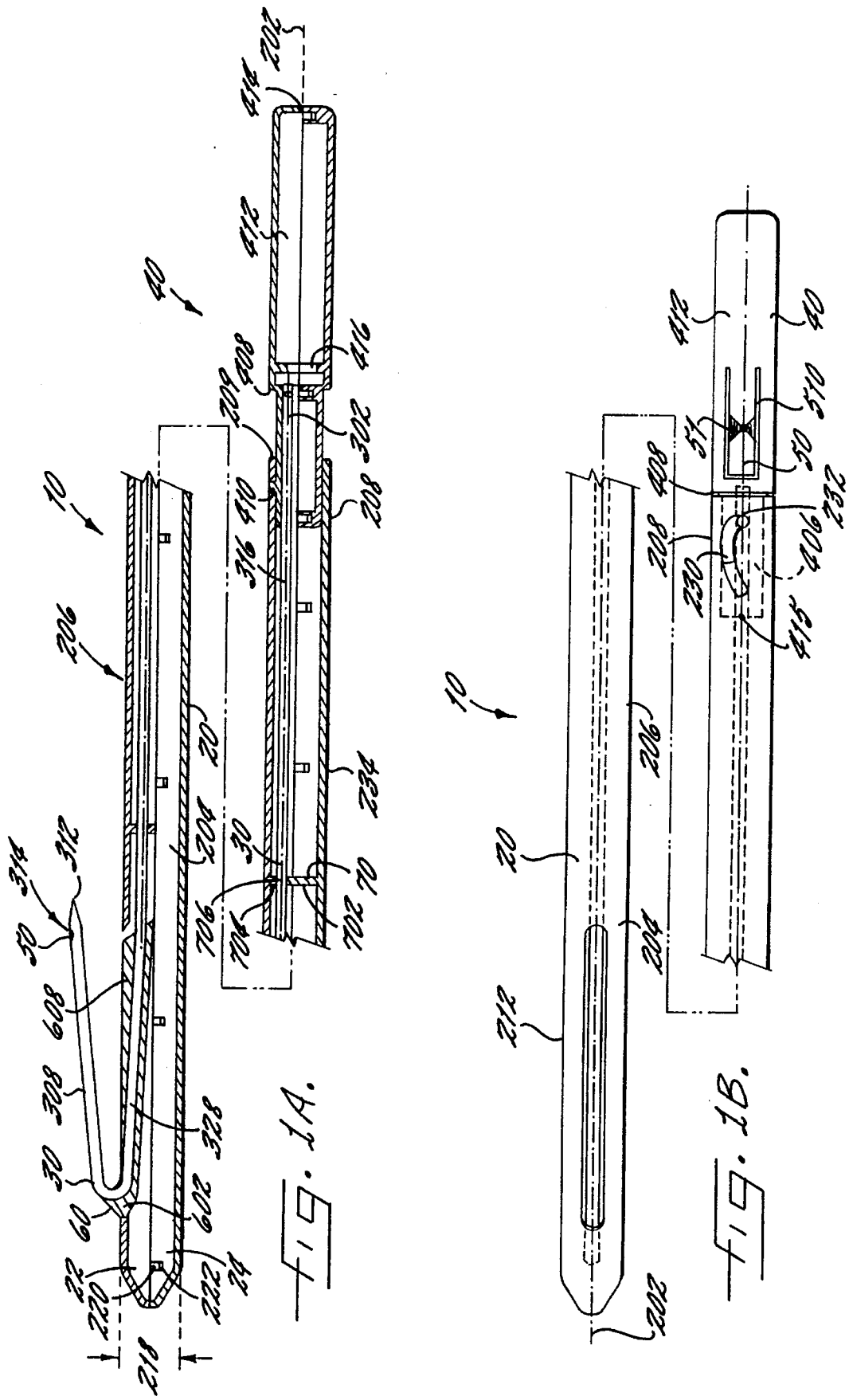

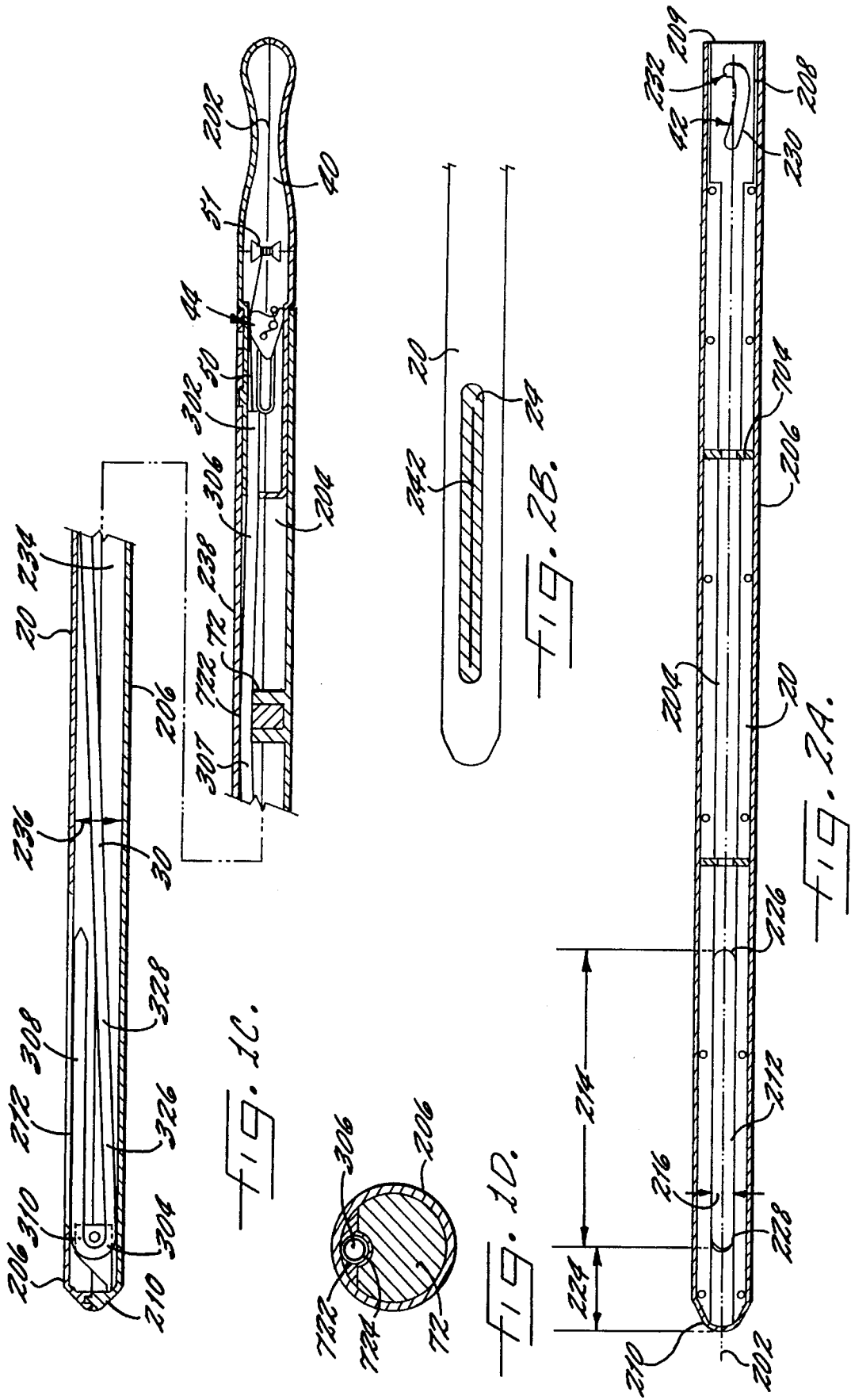

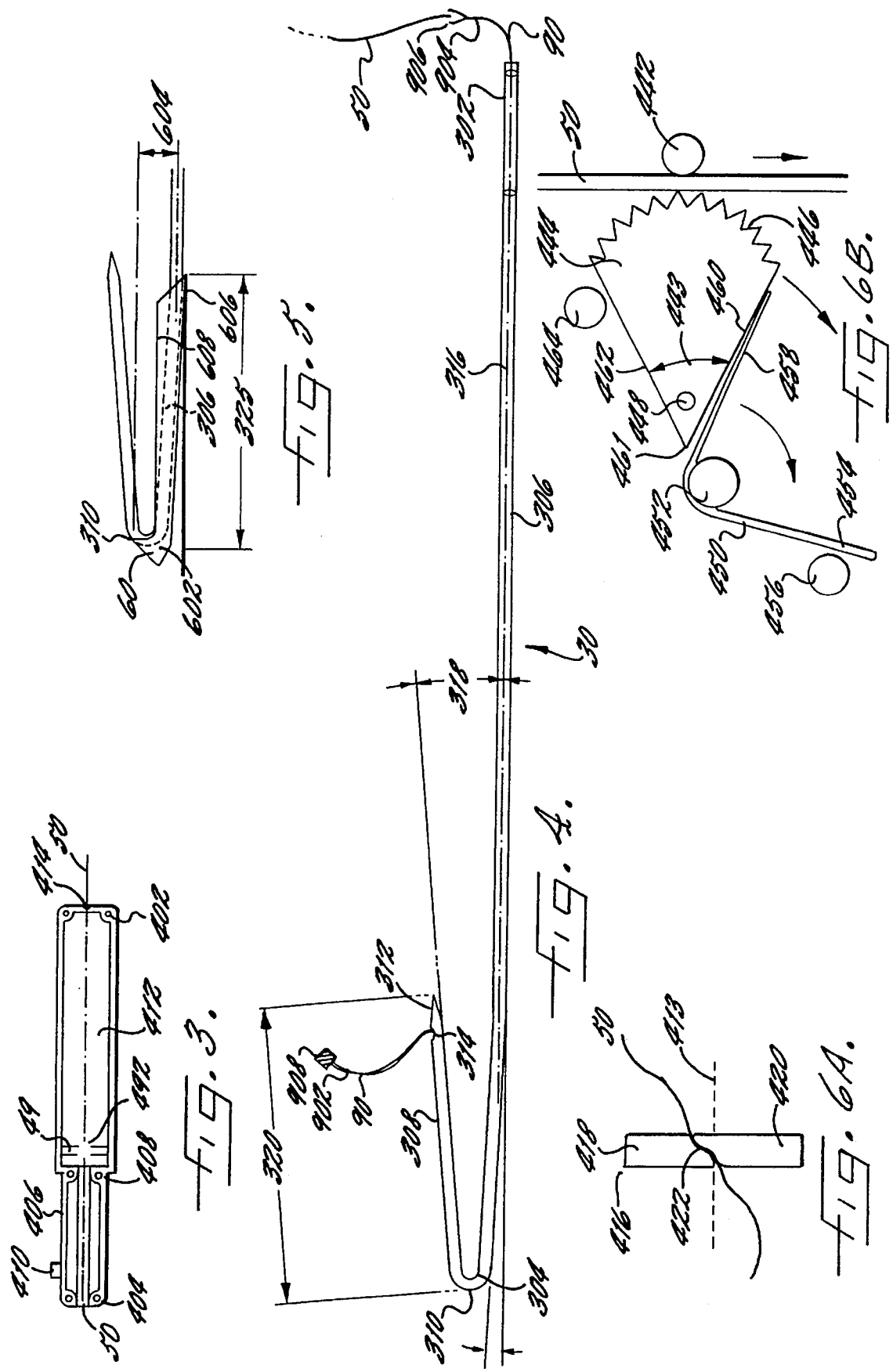

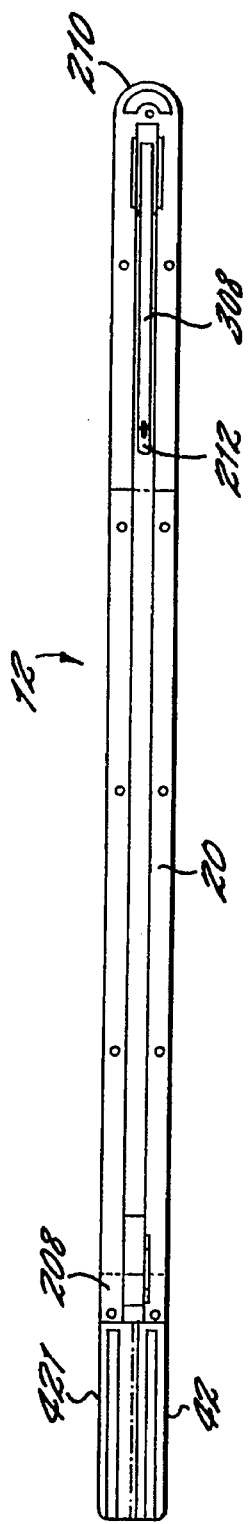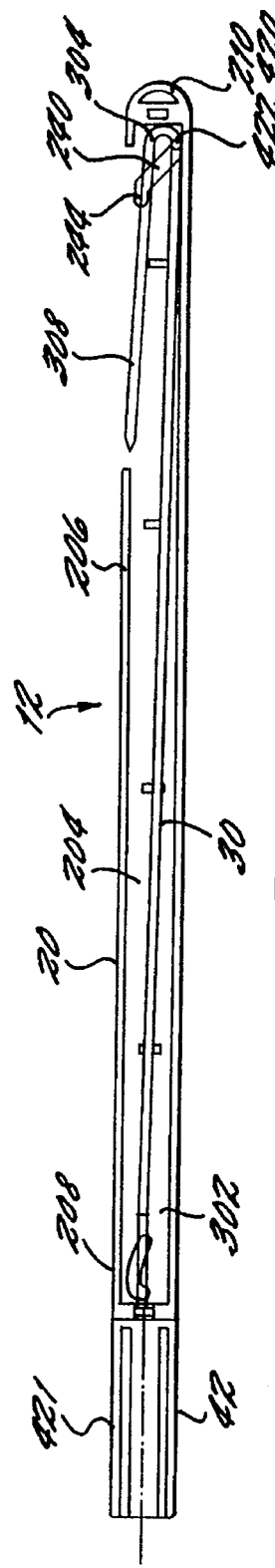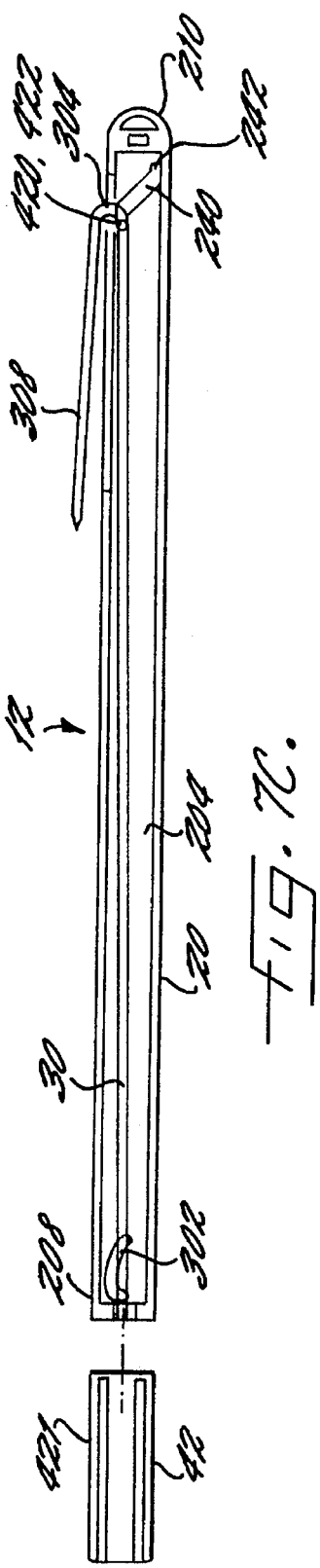

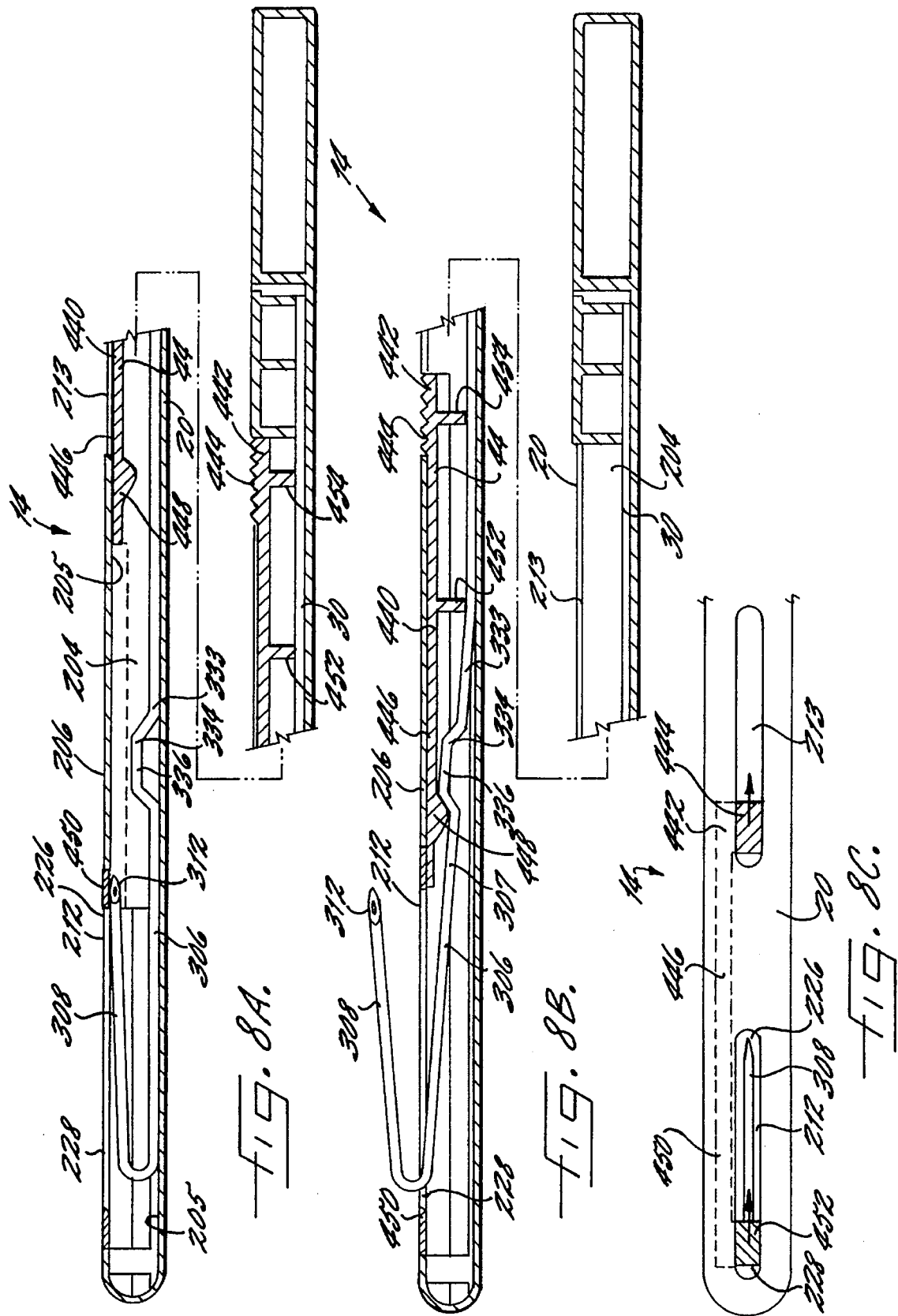

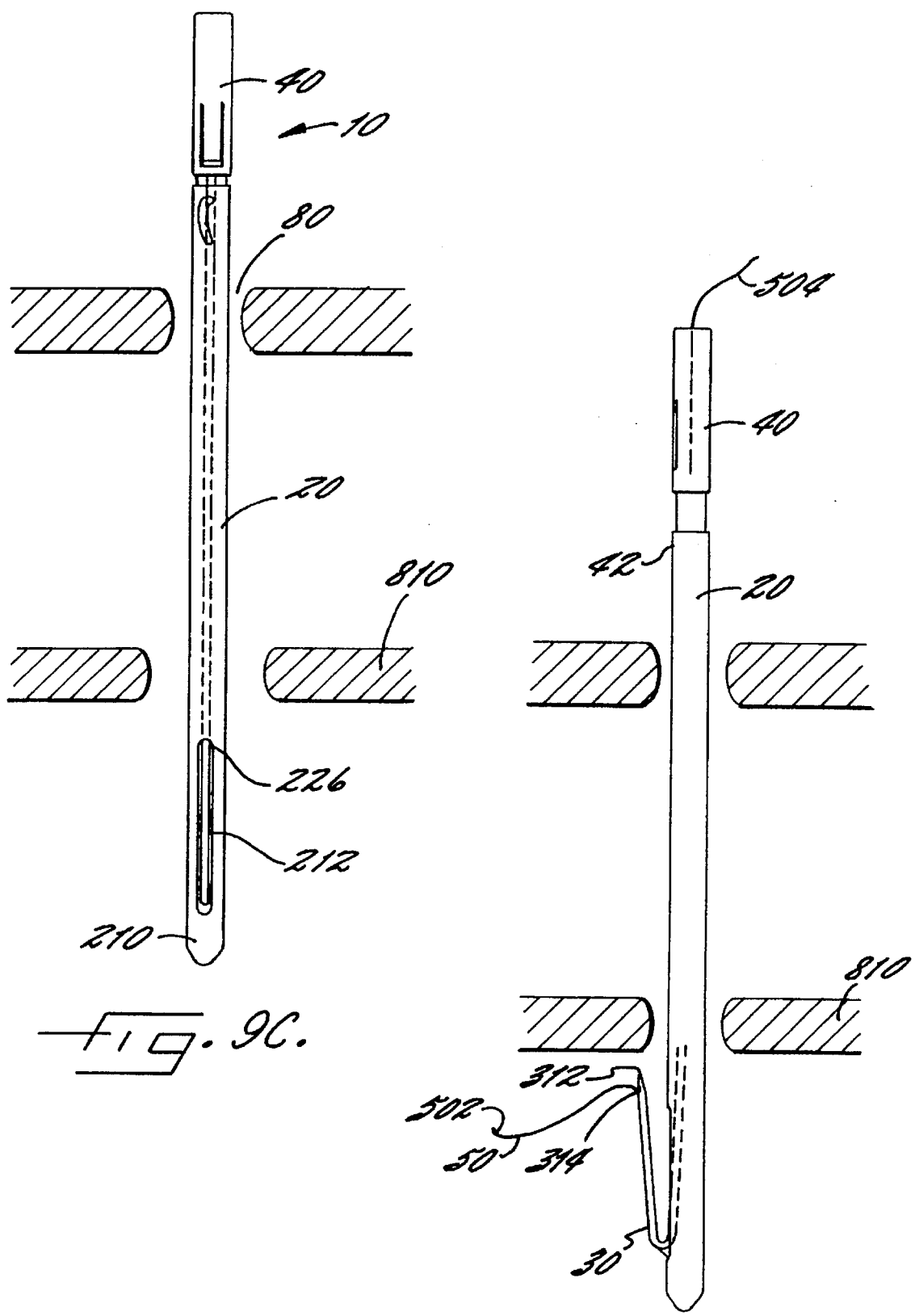

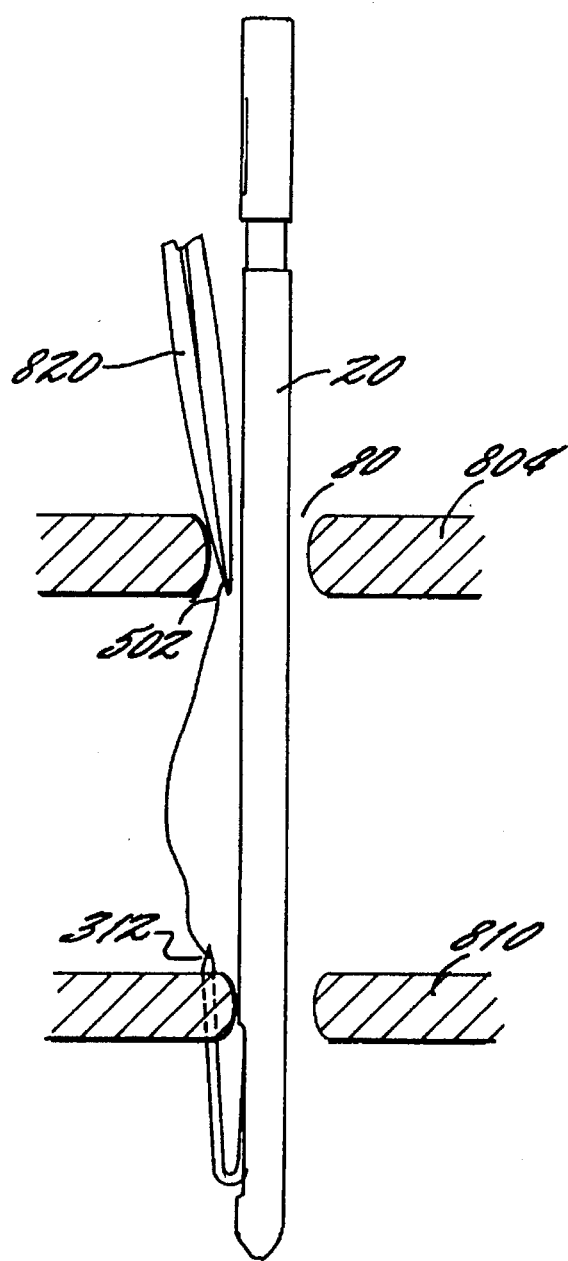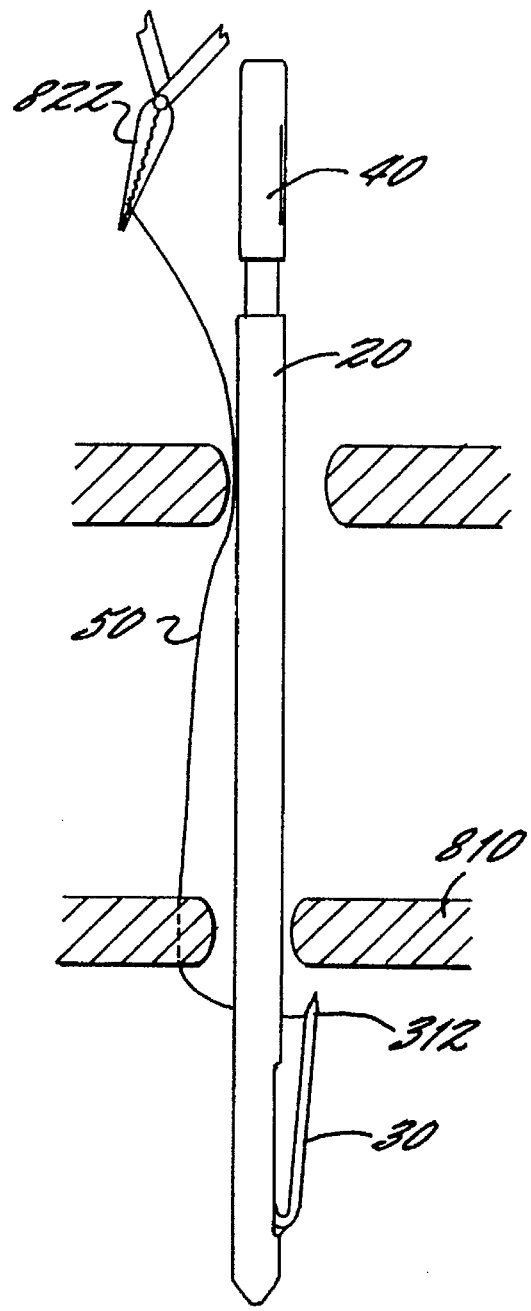
FIG. 9E.
FIG. 9F.

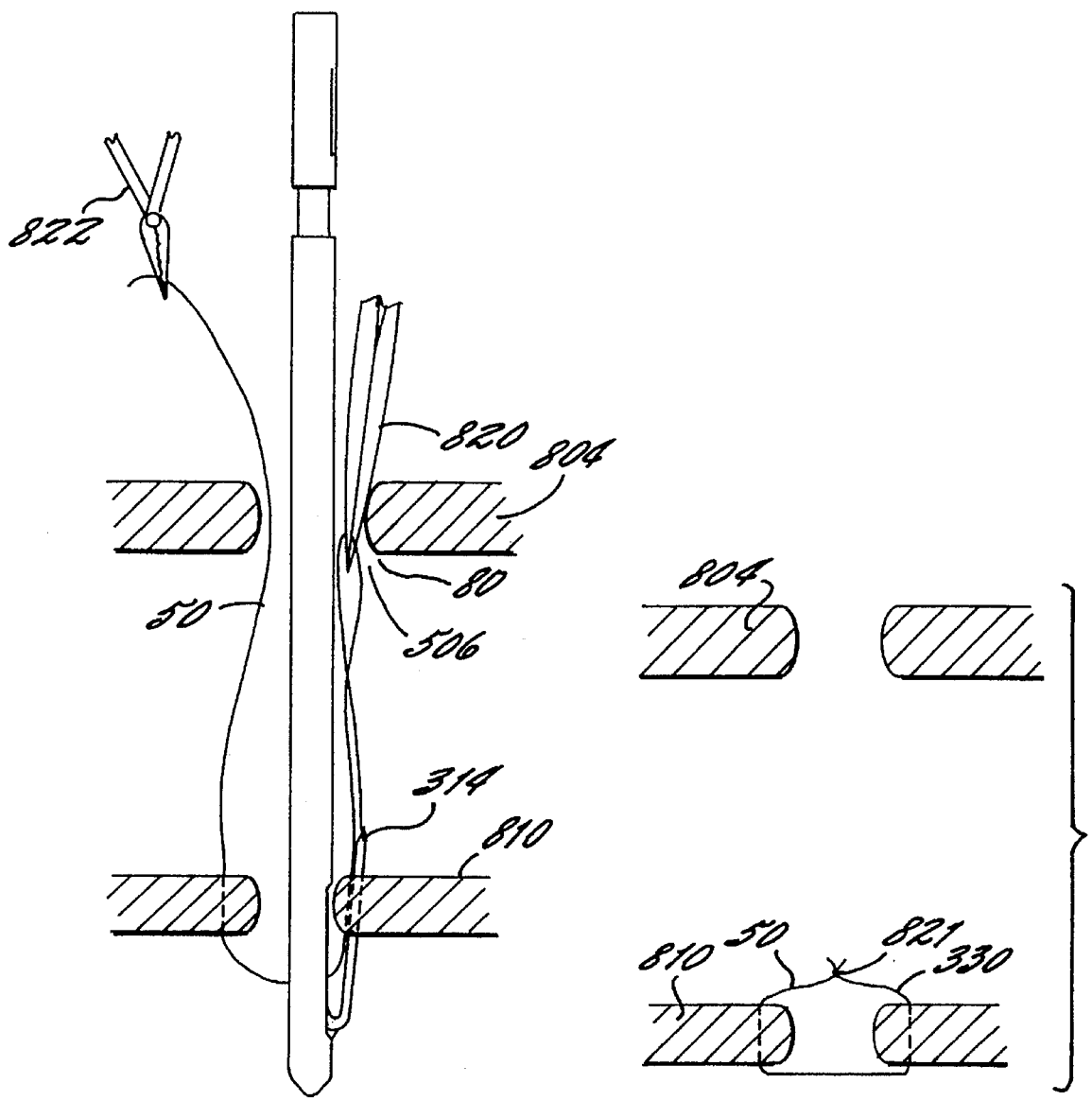

ENDOSCOPIC SUTURING DEVICE AND METHOD

CROSS-REFERENCE TO RELATION APPLICATIONS

This is a continuation-in-part of application "Surgical Stab Wound Closure Device and Method," U.S. Ser. No. 08/127,775, now U.S. Pat. No. 5,503,634 which is a continuation-in-part of "Surgical Stab Wound Closure Device and Method," U.S. Ser. No. 08/054,856, filed Apr. 28, 1993, now U.S. Pat. No. 5,350,385.

BACKGROUND OF THE INVENTION

1. Field of the Invention

This invention relates generally to the field of surgical devices and, more particularly, to surgical suturing apparati and methods of surgical suturing, specifically in laparoscopic and endoscopic applications.

2. Description of Related Art

Laparoscopic or endoscopic surgical procedures are now widely used in many specialties in the surgical community. These procedures generally involve a "C"-shaped incision through the navel through skin, adipose tissue fascia, muscle, and peritoneum, which comprise the abdominal wall or thoracic wall. Using this method many organs of the gut may be viewed and operated upon: gall bladder, intestines, appendix, uterus, fallopian tubes, ovaries, and lungs.

Trocars, pointed cannulae with pointed obturators for piercing the wall of a cavity, are often used to create ports through which surgical instruments nay be passed, instead of making long incisions in the abdominal or thoracic wall. The diameter of the trocar differs based upon the procedure to be performed, and may range from 3 to 33 millimeters.

Multiple trocars may be used so that a variety of instruments may be used simultaneously, such as a camera or magnifying lens, cutting, ligating, grasping, or suturing apparati. In this way, for example, forceps passed through gone trocar can grasp tissue while a cutting operation is performed through another, the whole procedure being visualized on a screen connected to a camera inserted into the cavity through a third trocar.

Such microsurgery techniques have made it necessary to perform wound closure on a much smaller scale than was required by the previously used large incisions. Up until now, multiple-layer closure has been utilized, whereby the entire abdominal wall has been sutured together to prevent evisceration or herniation of internal organs through the incision site. Should only the skin tissue be closed, complications can occur that include the viscera pushing up through the tissue. The tissue strangulates an organ that may get pushed up causing infection, peritonitis and possibly death.

Surgical suturing instruments, have been the subject of prior references. King (U.S. Pat. No. 373,372), McBrayer (U.S. Pat. No. 389,235), and Violante (U.S. Pat. No. 3,840, 017) disclose curved, hollow suture needles with suture thread positioned in and emerging from the bore and having a storage means for suture thread located within or upon a handle into which the suture needle is affixed. Violante's device further comprises a sharpened and beveled tip capable of cutting the suture thread when the procedure is completed. Karle (U.S. Pat. No. 2,327,353) described a device for surface wound stitching that utilizes two spools of suture thread for creating a lock stitch, not unlike that produced by a conventional sewing machine having a threaded needle that communicates with another spool of thread, the bobbin.

Baber's invention (U.S. Pat. No. 5,152,769) is specifically directed to a suture needle for laparoscopic procedures. His apparatus is designed for use with a trocar, and comprises a pair of concentric and slidable barrel portions. To the outer barrel is affixed a hollow suture needle having a curved tip and a hole through which suture thread may pass. A hook-shaped member is affixed to the inner barrel. Suturing is then accomplished by rotating the outer barrel to guide the needle through the tissue to be stitched and grasping the suture thread with the hook-shaped member to form a loop, which is held in place within the inner barrel until the next suture is made.

SUMMARY OF THE PRESENT INVENTION

It is an object of the present invention to provide a surgical suturing apparatus with Which it is possible to suture at least one subcutaneous layer of tissue.

It is an additional object to provide a method of suturing at least one subcutaneous layer of tissue.

It is a further object to provide such an apparatus that is insertable into a narrow incision in a position wherein the needle tip is covered, the tip being deployable from the apparatus proximal end after insertion.

These and additional objects are addressed by the device and method of the present invention, as will be described in the following.

The Surgical Suturing Apparatus

The surgical suturing apparatus of the present invention is directed to closing incisions penetrating a plurality of layers of tissue, particularly narrow incisions such as stab wounds or those formed by trocar punctures, such as those penetrating into the peritoneum.

This apparatus comprises a tubular body having a longitudinal axis, an inner space, a side wall, a first end, and a closed second end. The tubular body further has a slot through the side wall that communicates with the inner space having a length generally parallel to the longitudinal axis and a width. The slot is positioned generally adjacent the second end.

Within the inner space of the tubular body is housed a generally "J"-shaped suture needle. The suture needle has a distal end positioned adjacent the tubular body second end. The suture needle further has a first straight section and a second straight section, the first and the second straight sections each adjacent a curved middle section forming a generally "U"-shaped distal end. The first straight section is generally parallel to the longitudinal axis of the tubular body. The second straight section has a pointed tip and a suture gate dimensioned to allow suture material to pass therethrough, the suture gate being positioned along the second straight section adjacent the pointed tip. The second straight section has a length shorter than the length of the slot in the tubular body, enabling it to protrude therefrom when positioned adjacent thereto and moved in a radially outward direction.

In a preferred embodiment the tubular body second end is rounded to facilitate a smooth entry into the incision. The rounded nature of this portion enables suture needle entry that is not only easy to effect, but also causes no further tissue damage. Some prior art suturing devices having a pointed distal end can be difficult to insert and can tear tissue adjacent the incision while the surgeon is searching for the exact site to be sutured.

The apparatus further comprises suture needle deploying means affixed to the suture needle. The deploying means is movably engaged with the tubular body and is movable between a deployed position wherein the suture needle second straight section is positioned to protrude from the tubular body slot, and a closed position wherein the suture needle second straight section is positioned so as to be enclosed within the inner space of the tubular body.

In a preferred embodiment, the surgical suturing apparatus further comprises a first guiding means affixed to the suture needle for aiding the deploying means to move between the deployed and the closed positions. In addition, the apparatus in a preferred embodiment comprises a second guiding means affixed within the inner space of the tubular body for aligning the second straight section of the suture needle with the slot in the tubular body.

Method for Suturing Narrow Incisions

The method for utilizing the above-disclosed apparatus for suturing narrow incisions will now be described.

The method of the present invention comprises the steps of providing a surgical suturing apparatus as described above, and providing suture material threaded through the suture gate. The suture material has a first end emerging from the suture gate and a second end.

With the suture needle having been moved into the closed position, the tubular body of the surgical suturing apparatus is inserted into the incision, the second end of the tubular body inserted first. The tubular body is inserted sufficiently far that the top of the slot is positioned beneath the deepest tissue layer to be sutured.

The suture needle is deployed into the deployed position, such that the pointed tip protrudes from the tubular body beneath the deepest tissue layer to be sutured. The pointed tip is then positioned in a first suturing position, so that, when the tubular body is brought in a direction out of the incision sufficiently far that the pointed tip pierces the tissue layer to be sutured, the pointed tip extends above that layer.

Utilizing a forceps, the first end of the suture material is grasped and pulled out of the incision, and generally it is anchored so that it does not inadvertently get pulled back into the incision.

Next the tubular body is pushed back into the incision sufficiently far that the pointed tip is positioned beneath the tissue layer to be sutured, and the tubular body is rotated to position the pointed tip in a second suturing position, typically on the opposite side of the incision from the first suturing position. As previously, the tubular body is then brought in a direction out of the incision sufficiently far that the pointed tip pierces the tissue layer to be sutured and extends above it.

The suture material is then grasped, typically using forceps, at a location where the suture material is emerging from the suture gate, and is pulled out of the incision at the location grasped. Now with the two ends of the suture material having been brought out of the incision, a knot can be tied, thereby closing the incision in the tissue layer.

BRIEF DESCRIPTION OF THE DRAWINGS

A preferred embodiment of the invention along with alternate embodiments are described by way of example with reference to the accompanying drawings, in which:

FIG. 1 illustrates the surgical suturing apparatus of the present invention in (a) the deployed position and (b), (c) the closed position. In (c) a cross-sectional longitudinal view of an alternate subembodiment of the apparatus depicting two needle biases for aiding in deploying the suture needle. In (d) a radial cross-sectional view including the second guiding means and gasket is shown.

FIG. 2 depicts the tubular body of the surgical suturing apparatus (a) without and (b) with a sealing gasket.

FIG. 3 shows the deploying means of the surgical suturing apparatus.

FIG. 4 illustrates the suture needle of the surgical suturing apparatus.

FIG. 5 depicts the first guiding means affixed to the middle section of the suture needle.

FIG. 6 (a) and (b) show two embodiments of the tensioner housed in the deploying member.

FIG. 7 illustrates another embodiment having alternate deploying means, including cooperating camming elements. (a, b) The apparatus in the closed position and (c) the deployed position.

FIG. 8 (a), (b) illustrate side views in cross section of a third embodiment having alternate deploying means, including a slidable member that (a) covers the suture needle pointed tip in the closed position and (b) uncovers the suture needle pointed tip in the deployed position. (c) The third embodiment with the two slots in plan view.

FIG. 9(a)–(h) shows the method of using the surgical suturing apparatus with a suture needle bore in closing an incision in a deep tissue layer, including the exchange rod technique. Specifically, the steps include: (a) inserting a trocar; (b) inserting the tubular body into the trocar; (c) removing the trocar; (d) deploying the suture needle and positioning the pointed tip; (e) piercing a deep tissue layer, grasping and pulling out the suture material; (f) reinserting the tubular body and rotating it to position the pointed tip on the opposite side of the incision; (g) piercing the deep tissue layer, grasping and pulling out the suture material; (h) tying a knot.

DETAILED DESCRIPTION OF THE PREFERRED EMBODIMENT

Figure 9A:
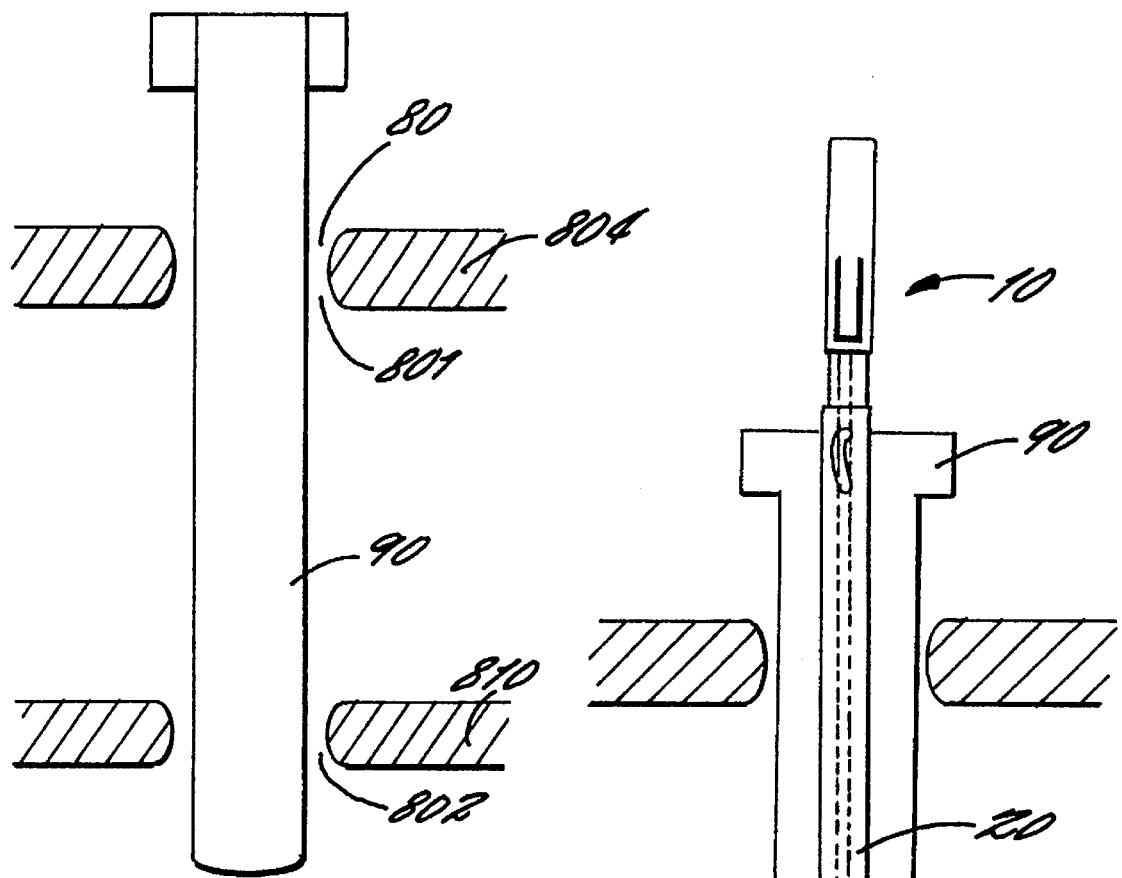

A description of the preferred embodiments of the apparatus and method of the present invention will now be presented with reference to FIGS. 1–12.

The Surgical Suturing Apparatus

Three preferred embodiments of the invention, a surgical suturing apparatus 10, useful in suturing stab wounds or narrow incisions as in the incision created by a trocar used in a laparoscopic or endoscopic surgical procedure, will be discussed. All of these embodiments contain certain common elements, which will be described with reference to FIG. 1. These common elements will retain the same numbering scheme throughout.

The preferred embodiments of the invention comprise a tubular body 20 having a longitudinal axis 202, an inner space 204, and a side wall 206. In the preferred embodiments the tubular body 20 is dimensioned to pass into a trocar puncture wound or alternatively into a surgical cannula. Therefore, a typical range of diameters 218 of tubular body 20 is 3–55 mm. For ease of manufacturing, tubular body 20 comprises two halves 22 and 24, generally semicircular in a cross section normal to longitudinal axis 202, that when assembled form a generally cylindrical body. The two halves 22 and 24 are affixed together via means known in the art such as complementary male and female elements 220 and 222 snap-fit together.

In an alternate assembly embodiment, the two halves may be fitted together in a bayonet-style mount, wherein the female element comprises a mating slot having a distal portion generally parallel to the longitudinal axis 202 and a generally perpendicular proximal portion. The mating in this embodiment is accomplished by sliding the male element into the distal portion of the mating slot generally in a direction parallel to the longitudinal axis 202 and the rotating the halves 22 and 24 relative to each other to snap and lock the male element into the proximal portion.

Tubular body 20 (see FIG. 2) further has a first end 208 and a closed second end 210. In a preferred embodiment second end 210 is rounded to facilitate a smooth entry into the incision. A slot 212 through the side wall 206 communicates with the inner space 204. Slot 212 has a width 216 and a length 214 generally parallel to the longitudinal axis 202. The slot 212, which has a top 226 and a bottom 228, is positioned generally adjacent the second end 210. The slot bottom 228 is separated from second end 210 by a distance 224.

In a subembodiment, shown in FIG. 2 (b), a gasket 24 covers slot 212. Gasket 24 has a slit 242 therein through which suture needle second straight section 308 may protrude when deployed.

Surgical suturing apparatus 10 further comprises a generally "J"-shaped suture needle 30 (see FIG. 4) dimensioned to reside within the inner space 204 of the tubular body 20. In a preferred embodiment suture needle 30 is formed of stainless steel; however, a combination of stainless steel with another material is also viable. Suture needle 30 has a distal end 304, which is positioned adjacent the tubular body second end 210. Suture needle 30 further has a first straight section 306 having a proximal end 302 and a second straight section 308, the first 306 and the second 308 straight sections each adjacent a curved middle section 310 forming a generally "U"-shaped distal end 304. The first straight section 306 is generally positioned along the tubular body longitudinal axis 202.

The second straight section 308 of suture needle 30 has a pointed tip 312 for piercing soft tissue. A suture gate 314, positioned along the second straight section 308 adjacent the pointed tip 312, is dimensioned to allow suture material 50 to pass therethrough.

In a preferred embodiment, suture needle 30 additionally has a bore 316 extending from the first straight section proximal end 302 to the suture gate 314, the bore being dimensioned to permit suture material 50 to pass therethrough.

Also in a preferred embodiment, the surgical suturing apparatus 10 further comprises a suture lead 90 for aiding in threading suture material 50 through the suture needle bore, the suture lead threaded through the bore 316 (see FIG. 4). The suture lead 90 has a distal end 902 that when loaded protrudes from the suture gate 314 ahd a proximal end 904 that protrudes from the suture needle first straight section proximal end 302. The suture lead proximal end 904 is affixable to the suture material 50, by, for instance, a small clamp 906. In use the suture material 50 is affixed to the suture lead proximal end 904, a tag 908 affixed to the suture lead distal end 902 is pulled from the suture gate 314 until the suture lead proximal end 904 and suture material 50 emerge from the suture gate.

The second straight section 308 has a length 320 shorter than the tubular body slot length 214, enabling the second straight section 308 to protrude outside the slot 212 when it is positioned adjacent thereto and moved in a radially outward direction.

The apparatus 10 additionally comprises suture needle deploying means 40 (see FIG. 3), which is affixed to the suture needle 30. The deploying means 40 has a first end 402 and a second end 404. The deploying means 40 is movably engaged with the tubular body 20 end is movable between a deployed position [FIG. 1 (a)] and a closed position [FIG. 1 (b)]. In the deployed position the suture needle second straight section 308 is positioned to protrude from the tubular body slot 212. In the closed position the suture needle second straight section 308 is positioned so as to be enclosed within the tubular body inner space 204.

Embodiment One. In this embodiment of apparatus 10, the first 306 and the second 308 straight sections are biased to flare away from a parallel orientation, shown in FIG. 4 as a flare angle 318, which typically lies in the range of 5–20 degrees. This bias causes the suture needle second straight section 308 to move radially and to protrude from the tubular body slot 212 when positioned adjacent thereto. The flaring bias also serves the purpose of providing a larger distance between the tubular body side wall 206 and the pointed tip when the suture needle is deployed, which will facilitate the suturing operation by permitting a larger "bite" of tissue to be taken.

Movement from the closed to the deployed position in this embodiment, which will be shown to be aided by a first 60 and a second 70 (or 72) guiding means, is achieved by pulling the deploying means 40, and thus the suture needle 30, in a proximal direction. As shown in FIG. 1, the tubular body inner space 204 has a diameter 236 that is generally normal to the longitudinal axis 202. Diameter 236 is dimensioned to closely engage the suture needle curved middle section 310, so that when it is positioned within the tubular body inner space 204, the suture needle first 306 and second 308 straight sections are pinched, preventing them from flaring away from a parallel orientation [see FIG. 1 (c)].

In use, then, when the deploying means 40 is in the closed position, the suture needle curved middle section 310 is positioned distal of the tubular body slot 212 within the tubular body inner space 204. As shown in FIG. 1 (c), the tubular body side wall 206 pinches the suture needle curved middle section 310, forcing the suture needle second straight section 308 within the tubular body inner space 204.

When the deploying means 40 is pulled into the deployed position, as shown in FIG. 1 (a), the suture needle 30 is moved in a proximal direction relative to the tubular body 20 until the suture needle curved middle section 310 and the second straight section 308 are both positioned adjacent the tubular body slot 212. In this position the suture needle curved middle section 310 is released from pinching relation with the tubular body side wall 206. The suture needle bias then causes the suture needle second straight section 308 to protrude from the slot 212.

The apparatus 10 may also be designed without a flare (the case of 0 degrees flare angle 318).

The suture needle first straight section 306 is somewhat pliable and is biased to a substantially linear orientation, so that, if bent, it tends to return to linear. This biasing is also used in deploying the suture needle second straight section 308 by cocking the suture needle first straight section 306 away from linear when the deploying means 40 is in the closed position, providing a potential energy to aid in releasing the first straight section 306 from the tubular body, slot 212.

In order to accomplish this, the tubular body 20 shown in FIG. 1 (*c*) further comprises a second guiding means 72 affixed within the tubular body inner space 204 that assists in aligning the suture needle second straight section 308 with the tubular body slot 212. The second guiding means 72 comprises an element affixed alone a central portion 234 of the tubular body inner space 204 and is positioned to restrain a central portion 307 of the suture needle first straight section 306 generally along a central section 238 of the tubular body side wall 206. The first straight section central portion 307 is restrained generally in longitudinal alignment with the tubular body slot 212 to effect the alignment.

This structure functions so that, when the suture needle deploying means 40 is in the closed position, as shown in FIG. 1 (*c*), a distal end 326 of the suture needle first straight section 306 is restrained adjacent the tubular body side wall 206 generally opposite the tubular body slot 212. In this position the suture needle first straight section 306 is bent away from a linear orientation and away from the tubular body slot 212.

When the suture needle deploying means 40 is moved to the deployed position, the suture needle first straight section 306 bias tends to return the suture needle first straight section 306 to a generally linear orientation, wherein its distal portion 328 is generally adjacent the tubular body slot 212, the suture needle second straight section 308 is released to enable it to protrude from the tubular body slot 212.

In order to assist in retaining gas pressure within the body cavity, a sealing means is provided in the form of a gasket 722 encompassing the space between the element 72 comprising the second guiding means and the tubular body inner space 204, as shown in cross section in FIG. 1 (*d*). Gasket 722 has a hole 724 therein dimensioned to closely engage suture needle first straight section 306 and prevent gas from escaping through the apparatus 10.

In a particular configuration the tubular body has an opening 209 at the first end 208. The deploying means (FIG. 3) has a hollow inner space 412, a first end 402, and a second end 404, which has a generally cylindrical distal portion 406 dimensioned to engage and slide within the tubular body first end opening 209. The deploying means 40 further has a shoulder 408 adjacent to and proximal of the distal portion 406 dimensioned larger than the tubular body first end opening 209. This dimensioning permits the deploying means distal portion 406 to slide into the tubular body first end opening 209 until the sliding is stopped by the shoulder 408. In this case the closed position comprises a position wherein the shoulder 408 is in a position adjacent the tubular body first end 208.

In one embodiment wherein su Cure needle 30 has a bore 316, the deploying means 40 has a hollow inner space 412 and holes 414, 415 through the first 402 and second ends 404, respectively, dimensioned to permit suture material 50 to pass therethrough. During use, then suture material 50 is threaded through the hole 414, through the deploying means inner space 412, through hole 415, into the suture needle bore 316, and out the suture gate 314.

In another embodiment shown in FIG. 1 (*b*), suture needle 30 also has a bore 316, and the deploying means 40 has a hollow inner space 412 and a hole 415 through the second end 404 dimensioned to permit suture material 50 to pass therethrough. In this case the deploying means 40 further comprises means for holding a bobbin 51 of suture material 50 within the deploying means inner space 412. Specifically, bobbin holder 510 is adapted to permit bobbin 51 to snap fit thereonto. In use, then suture material 50 is unwound from bobbin 51, threaded through hole 415, into suture needle bore 316, and out the suture gate 314.

In addition, tensioner means 416 are affixed within the deploying means inner space 412 for maintaining constant tension on suture material 50 passing through the deploying means inner space 412 and further for retarding movement of suture material 50 passing in a proximal direction. As shown in FIGS. 1 (*a*) and 6 (*a*), a particular embodiment of the tensioner means 416 comprises two closely fitting members 418 and 420, each affixed within the inner space 412, the members 418 and 420 defining a channel 422 therebetween. The channel 422 is configured sufficiently wide to permit suture material 50 to slide therebetween but sufficiently narrow to maintain a tautness in the suture material 50. Additionally, channel 422 is generally noncollinear with line 413 between the hole 414 through which the suture material 50 enters and the proximal end 302 of the suture needle 30, into which suture material 50 enters the bore 316. Thus channel 422 creates an additional impediment to the suture material's 50 unrestricted passage.

A gasket 49 affixed within the deploying means inner space 412 and positioned generally adjacent the deploying means shoulder 408 provides an alternate means of providing tension to the suture material 50 (see FIG. 3). Gasket 49 has a hole 492 therein dimensioned to restrict suture material 50 movement and also to prevent gas leakage through the instrument when in use, thus providing an additional means of maintaining pneumoperitoneum, for instance, during surgery.

Another embodiment 44 of the tensioner means is shown in FIG. 6 (*b*). A fixed element, here a post 442, is affixed within the deploying means inner space 412. In spaced relation to the post 442 is affixed a pivotable element, here a pawl 444, that has a jagged curved edge 446 and pivots about pivot 448. The jagged edge 446 is generally opposite the post 442 and aids in restraining the suture material 50 passing between the post 442 and the pawl 444. Alternatively, the fixed element could comprise the interior of deploying means inner space 412, as shown in FIG. 1 (*c*).

The pawl 444 is generally shaped like a "pie slice," having a first 460 and a second 462 generally straight side meeting at an angle 443 generally in the range of 30–90 degrees. The jagged curved edge 446 generally describes an arc connecting the two sides 460, 462. The pivot 448 is generally positioned adjacent the corner 461 at which the sides 460, 462 meet, and the first side 460 is generally distal of the second side 462.

The pawl 444 in general is movable between a locking position wherein suture material 50 positioned between the post 442 and the pawl 444 is restrained from moving and a releasing position wherein suture material 50 passing between the post 442 and the pawl 444 is generally freely movable therebetween. In the embodiment shown, the pawl 444 pivots generally in a distal direction, shown by the arrows in FIG. 6 (*b*), when moving from the locking to the releasing position.

The pawl 444 is biased to the locking position by a torsion spring 450, affixed at center 452 within the deploying means inner space 412 generally adjacent and distal of pawl corner 461. A first side 454 of torsion spring 450 is braced against second post 456, which is also affixed within the deploying means inner space 412. A second side 458 of torsion spring 450 is braced against the pawl first side 460, thereby providing the biasing to the locked position.

In order to limit the movement of the pawl 444 caused by the torsion spring 450, a stop 464 is provided that is also affixed within the deploying means inner space 412. The stop 464 is positioned to limit the movement of the pawl 444 caused by the torsion spring 450 by bracing the pawl second side 462 against further proximal movement.

In use, when the suture material 50 is pulled in the distal direction, the suture material 50 engages the pawl's jagged curved edge 446, causing the pawl 444 to pivot, to compress the torsion spring 450, and to move into the releasing position, permitting the suture material 50 to pass in the distal direction.

In a preferred embodiment, deploying means 40 also includes a stop means 42 for preventing a disengagement of the deploying means 40 and the tubular body 20. In a particular embodiment of the stop means 42, the tubular body side wall 206 has an inner channel 230 adjacent the first end 208. This channel 230 communicates with the inner space 204, but does not extend completely through the side wall to the outside, and has a proximal end 232. The stop means 42 in this case comprises a protrusion 410 adjacent the deploying means second end 404, wherein the protrusion 410 is dimensioned to slide within the channel 230 during a movement of the deploying means 40 relative to the tubular body 20.

In use, when the deploying means 40 is moved into the deployed position, the protrusion 410 reaches the proximal end 232 of the channel 230 and prevents further extension of the deploying means 40 in a proximal direction, thereby retaining the first end 402 of the deploying means 40 within the tubular body 20.

In a preferred embodiment, apparatus 10 further comprises a first guiding means 60 affixed to the suture needle 30 for aiding the deploying means 40 to move between the deployed and the closed positions. An exemplary first guiding means 60 is affixed along the suture needle's curved middle section 310 and first straight section 306. The first guiding means 60, shown in FIG. 5, in the preferred embodiment comprises a molded plastic member surrounding the curved middle section 310 and a distal section 324 of the first straight section 306. First guiding means 60 has a distal end 602 extending distalward of the suture needle curved middle section 310, this distal end 602 dimensioned to remain within the tubular body inner space 204 when the deploying means is in the deployed position. The first guiding means 60 further has a width 604 generally parallel to a plane formed by the first 306 and the second 308 straight sections of the suture needle 30. The width 604 generally tapers downward toward the distal end 602, wherein in use the taper aids the movement of the deploying means 40 from the deployed to the closed position by ramping the suture needle curved middle section 310 into the tubular body inner space 204.

Additionally, first guiding means 60 has a proximal portion 606 that has a protrusion 608, at least part of which is positioned adjacent the suture needle first straight section distal portion 328 and extends in a direction toward the tubular body slot 212. Protrusion 608 has sufficient length 325 and width that, when the deploying means 40 is in the deployed position, protrusion 608 plugs slot 212, thereby preventing tissue material from entering the tubular body inner space 204 and also preventing gases from escaping from the body cavity through the apparatus.

In order to prevent a further movement of the suture needle 30 in the proximal direction after the deploying means 40 has reached the deployed position, means are provided for restricting such movement [see FIG. 1 (a)]. To this end, the first guiding means protrusion 608 has a ramp 607 at the proximal end 609, and the tubular body side wall 206 also has a ramp 207 adjacent the top 226 of the slot. Side wall ramp 207 is dimensioned to engage the first guiding means protrusion ramp 607 when the deploying means 40 is in the deployed position and to prevent a further movement of the suture needle 30 in a proximal direction.

In order to further protect slot 212, the length 320 of suture needle second straight section 308 is dimensioned sufficiently close to the slot length 214 that, when the deploying means 40 is in the closed position, second straight section 308 plugs slot 212, again preventing tissue material from entering the tubular body inner space and also preventing gases escaping from the body cavity through the apparatus 10.

Apparatus 10 in the embodiment shown in FIG. 1 (a) further comprises another embodiment of the second guiding means 70 affixed within the tubular body inner space 204 for aligning the second straight section 308 of the suture needle with the tubular body slot 212 [FIG. 1 (a)]. In a specific embodiment, the second guiding means 70 comprises an element 702 affixed along a central portion 234 of the tubular body inner space 204. Element 702 has a hole 704 that has a longitudinal axis 706 generally parallel to the tubular body longitudinal axis 202. The hole 704 is dimensioned to permit the suture needle first straight portion 306 to slide therethrough, thereby providing support to the suture needle 20. The positioning of element 702 and hole 704 also ensures a correct alignment of the suture needle 30 relative to the tubular body slot 212.

Embodiment Two. In this embodiment of apparatus 12, illustrated in FIG. 7 (a)–(c), the deploying means 42 comprises a deploying member affixed to the suture needle 30 that has an operating portion 421 exterior to the tubular body 20. The deploying member is in one embodiment similar to the deploying means 40 shown in FIG. 1, wherein movement between the deployed and closed positions is accomplished by moving the deploying member, which is affixed to the suture needle proximal end 302 and is movable in and out of the tubular body first end 208.

Deploying means 42 further comprises a camming member 420 affixed at least partially within the tubular body inner space 204 to the suture needle 30 and having a radially extending protrusion 422. In a particular embodiment, camming member 420 is affixed adjacent the suture needle distal end 304.

Tubular body 20 further comprises a camming slot 240 communicating with the tubular body inner space 204 dimensioned and adapted to slidably engage the camming member protrusion 422. In the particular embodiment shown in FIG. 7 (a) and (b), the camming slot 240 is positioned adjacent the tubular body second end 210. The camming slot 240 has a first end 242 and a second end 244, and the camming member 420 and camming slot 240 are positioned so that, when the camming member protrusion 422 is positioned at the camming slot first end 242, the suture needle second straight section 308 is enclosed within the tubular body inner space 204. Further, they are positioned so that, when the camming member protrusion 422 is positioned at the camming slot second end 244, the suture needle second straight section 308 is deployed through the tubular body slot 212 ant outside the tubular body side wall 206.

The operation of this embodiment can thus be seen to be accomplished by utilizing the deploying member to manipulate the suture needle into the desired position, the cooperating camming elements 422 and 240 serving to orient the suture needle second straight section 308 in the correspondingly desired position.

Embodiment Three. In this embodiment of apparatus 14, shown in FIG. 8, the deploying means 44 utilizes a sliding member to cover a portion of the needle when the closed position is desired [FIG. 8 (a)] and to permit the needle to protrude when the deployed position is desired [FIG. 8 (b)].

Specifically, in this embodiment, the first 306 and the second 308 straight sections of the suture needle 30 are biased to flare away from a parallel orientation.

In addition, a distal portion 307 of the first straight section 306 is biased to curve in a direction toward the second straight section 308. Thus, when the deploying means 44 is moved into the deployed position, wherein the suture needle second straight section 308 is positioned adjacent the tubular body slot 212, the suture needle biases cause the second straight section 308 to protrude therefrom.

A central portion 333 of the first straight section 306 of the suture needle 30 has a ramp 334 therein. A top part 336 of the ramp 334 extends in a direction generally toward the tubular body side wall 206 adjacent the tubular body slot 212.

Further, the deploying means 44 comprises a longitudinally slidable covering means 440 having several sections. A proximal section 442 comprises means exterior to the tubular body 20 for effecting a sliding of the covering member 440 relative to the tubular body 20. An exemplary proximal section 442 comprises a ridged member 444 that protrudes through a second slot 213 in the tubular body 20 generally collinear with slot 213 and slides therealong, usually with thumb pressure.

A central section 446 of covering means 440 extends generally along an inner wall 205 of the tubular body inner space 204 proximal of and generally longitudinally aligned with the tubular body slot 212 [see FIG. 8 (c)]. The central section 446 has a protrusion 448 adapted to be adjacent to and distal of the suture needle ramp 334 when the deploying means 44 is in the deployed position and to be proximal of the suture needle ramp 334 when the deploying means 44 is in the closed position. A cooperative action between the suture needle ramp 334 and the protrusion 448 when moving the deploying means 44 from the deployed to the closed position serves to push the suture needle first straight section 306 toward the tubular body inner wall 205 radially opposite the tubular body slot 212, thereby moving the suture needle distal end 304 within the tubular body inner space.

A distal section 450 of covering means 440 comprises means 452 covering a portion of the tubular body slot 212 and is slidable relative thereto. The distal section 450 is adapted to be positioned adjacent a bottom 228 of the slot 212 when the deploying means 44 is in the deployed position. This permits the suture needle first 306 and second 308 straight sections to flare away from each other. The distal section 450 is further adapted to be positioned adjacent a top 226 of the slot 212 when the deploying means 44 is in the closed position, covering the suture needle pointed tip 312 and preventing the suture needle first 306 and the second 308 straight sections from flaring. This is accomplished by dimensioning the slot 213 to be at least as long as slot 212.

In a particular embodiment, the covering member central section 446 further has a brace, as shown, two braces 452 and 454, proximal of the protrusion 448. These braces 452, 454 extend radially across the tubular body inner space 204 to restrain a central portion 333 of the suture needle first straight section 306 against the tubular body inner wall 205 radially opposite and proximal of the tubular body slot 212. These braces 452, 454 thus restrain the bias in the distal portion of the suture needle first straight section 306 at the points of contact therebetween.

Methods of Suturing a Narrow Incision in a Subcutaneous Tissue Layer

The above-disclosed apparatus 10 may be used in any laparoscopic or endoscopic application. For purposes of illustration, however, its use will be described for suturing a small incision associated with a trocar puncture in the abdomen.

Figure 10:
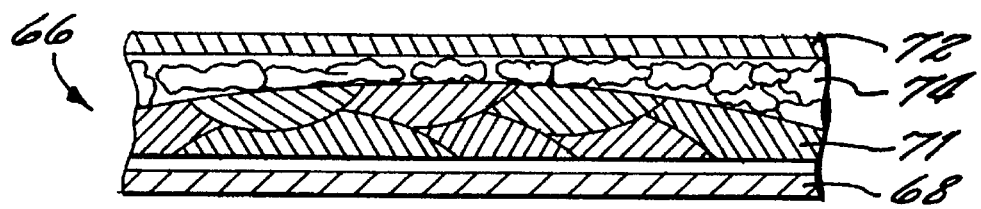
FIG. 10 shows typical tissue layers atop a body cavity.

Method Embodiment One. With reference to FIG. 10, it can be seen that the abdominal wall 66 comprises the peritoneum 68, a layer of muscle tissue 71, and the cutaneous layer 72. The subcutaneous fat 74 layer is not sutured.

The method for utilizing the above-disclosed apparatus 10 for suturing a narrow incision 80 will now be described with reference to FIG. 9 (d)–(h). Incision 80 comprises an incision 801 in the cutaneous layer 804 and at least one incision 802 in a subcutaneous layer 810.

A surgical suturing apparatus 10 as described above in Embodiment One is provided, threaded with suture material 50. In a particular embodiment, suture material 50 is threaded through the suture gate 314, the suture material 50 having a first end 502 emerging from the suture gate 314 and a second end 504. Typically tubular body 20 is held in the surgeon's nondominant hand, and forceps 820 are manipulated with the dominant hand.

Figure 9B:
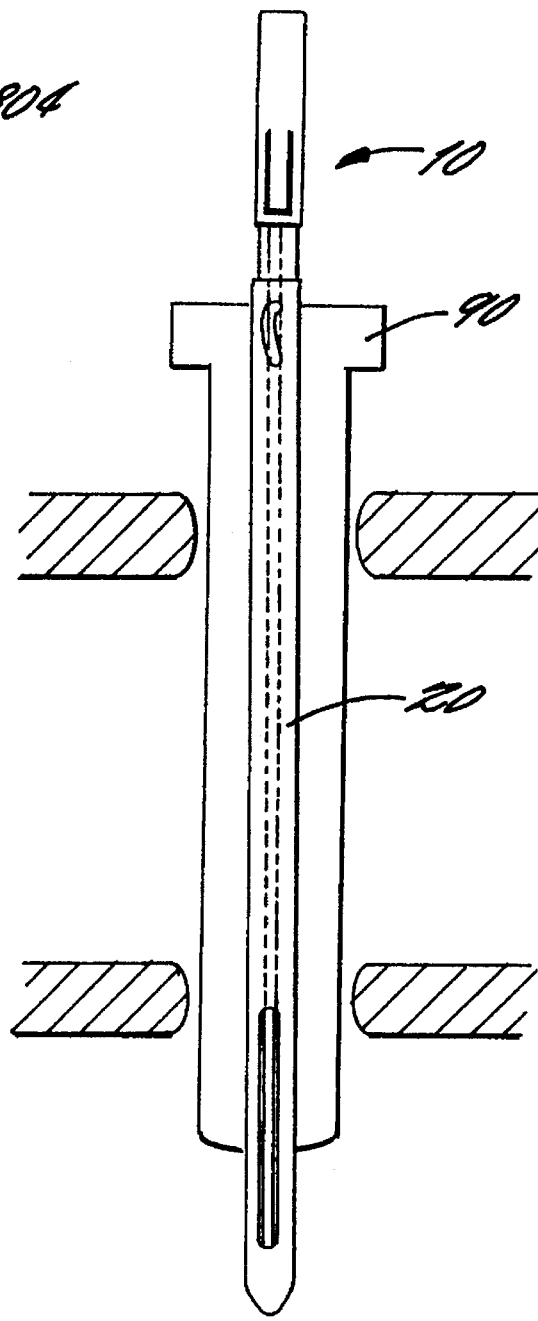

With the deploying means 40 in the closed position, that is, with the suture needle 30 completely enclosed within the tubular body inner space 204, and therefore with pointed tip 312 and suture gate 314 also covered, the tubular body 20 is inserted into the incision 80, the second end 210 inserted first, sufficiently far that the top 226 of the slot 212 is positioned beneath the deepest tissue layer 810 to be sutured [FIG. 9 (c)].

Next the suture needle 30 is deployed by the deploying means 40 into the deployed position, in the preferred embodiment by pulling the deploying means 40 away from the tubular body 20 until the stop 42 is reached. In this position the pointed tip 312 protrudes from the tubular body 20 beneath the deepest tissue layer 810 to be sutured [FIG. 9 (d)].

The pointed tip 312 is then positioned in a first suturing position, and the tubular body 20 is brought in a direction out of the incision 80 sufficiently far that the pointed tip 312 pierces the tissue layer 810 to be sutured and extends thereabove, while avoiding impaling the cutaneous layer 804 [FIG. 9 (e)].

Using a grasping means such as a forceps 820, the first end 502 of the suture material 50 is grasped and is pulled out of the incision 80. Typically the, first end 502 is then secured with an implement such as a hemostat 822.

Next the tubular body 20 is pushed in a direction into the incision 80 sufficiently far that the pointed tip 312 is positioned beneath the tissue layer 810 to be sutured. Then the tubular body 20 is rotated to position the pointed tip 312 in a second suturing position [FIG. 9 (f)].

As previously, the tubular body 20 is brought in a direction out of the incision 80 sufficiently far that the pointed tip 312 pierces the tissue layer 810 to be sutured and extends thereabove, again avoiding impaling the cutaneous layer 804 [FIG. 9 (g)].

Again the suture material 50 is grasped, this time at a location 506 where the suture material 50 is emerging from the suture gate 314 and it is pulled out of the incision at the location 506 grasped. At this point the suture material may be secured with a hemostat 822, or a knot may be tied to close the incision 802 in the subcutaneous tissue layer 810 after removing the apparatus 10 from the incision 80.

If a cut length of suture material has been used, the knot 821 can be tied using the two ends secured by hemostats 822 [FIG. 9 (h)]. If a bobbin 51 has been used from which to feed suture material 50 out through the suture gate 314 from needle bore 316, it can be cut at location 506 prior to tying the knot.

The above procedure may be repeated on the same layer of tissue to form multiple sutures, such as in the form of an "X" or a plurality of parallel sutures.

Figure 11:
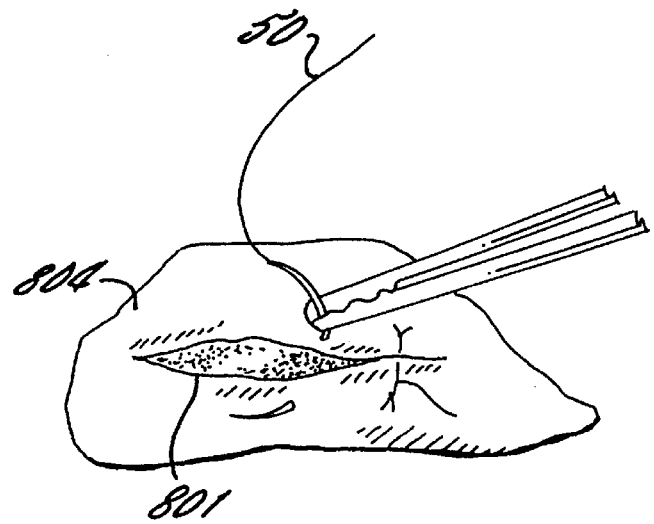
FIG. 11 shows the closing of the skin layer.

The procedure may also be repeated on successively more shallow layers of tissue until all but the cutaneous layer are closed, the final step of the closure comprising suturing the cutaneous layer by conventional means, such as shown in FIG. 11. Such a conventional closure of incision 80 in cutaneous layer 804 may comprise, for instance making multiple surface sutures 840 along incision 801 with the use of suture needle 88, suture material 50, and forceps 820.

Figures 12A, 12B:
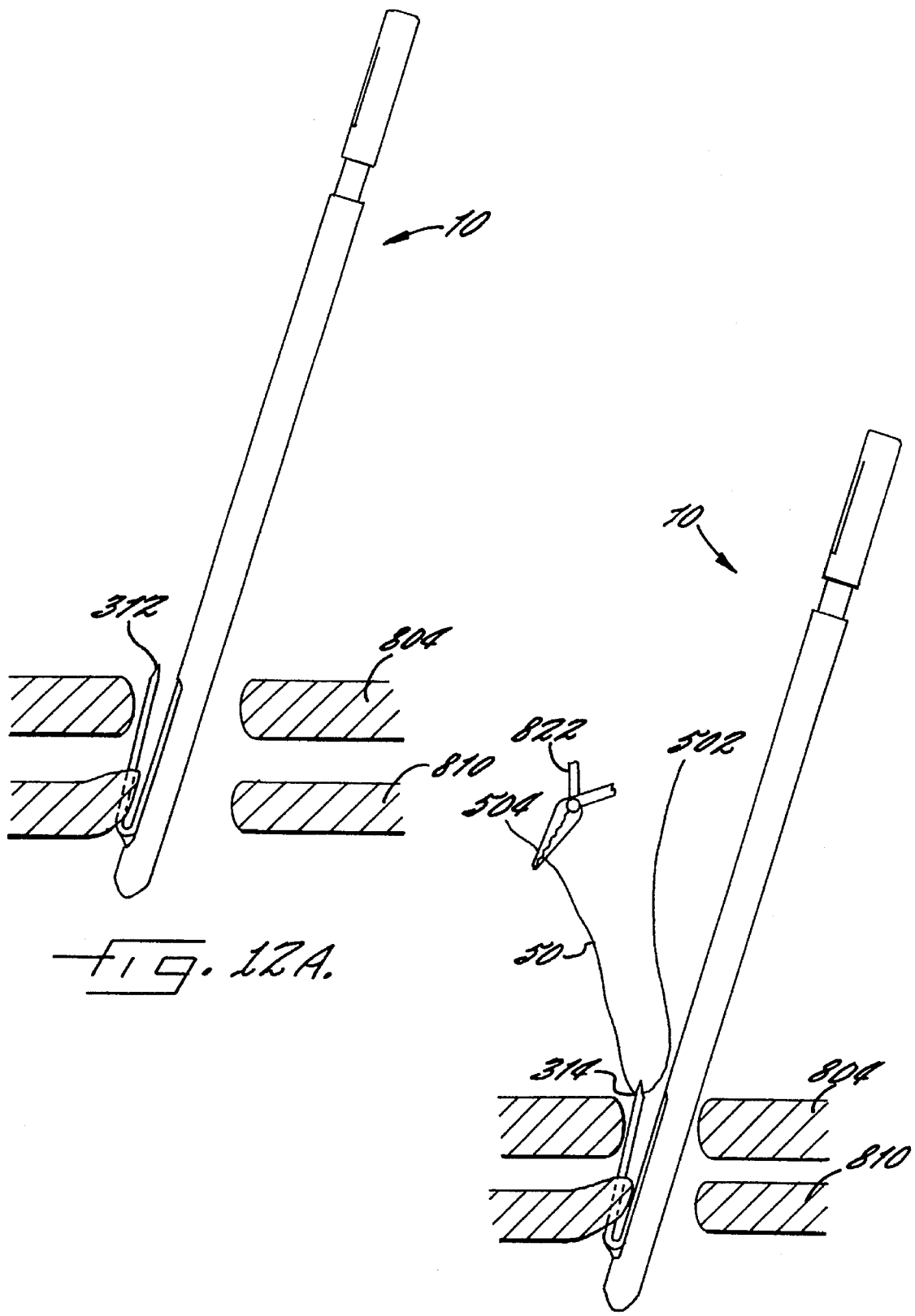
FIG. 12(a)–(b) shows a method of using the surgical suturing apparatus without a suture needle bore in closing an incision in a deep tissue layer. The steps that differ from those shown in FIG. 9 include: (a) pulling the tubular body out of the incision to expose the pointed tip; (b) threading the needle and grasping an end.

Method Embodiment Two. Using an embodiment of apparatus 10 not having a bore through the Suture needle, a similar method may be undertaken wherein suture material is threaded into suture gate 314 after deploying the suture needle 30 from out of the tubular body 20. In FIG. 12 are shown only the additionally needed steps for external threading, since the remaining steps are substantially the same as those shown in FIG. 9.

In this embodiment, the suture material providing step is not present. Instead, following the first bringing of the tubular body 20 out the incision 80, the tubular body 20 is brought further out of the incision 80 to expose the pointed tip 312 above a cutaneous layer 804, avoiding piercing the cutaneous layer 804 with the pointed tip 312 [FIG. 12 (a)]. Then a first end of suture material 502 is threaded through the suture gate 314, and a second end 504 of the suture material 50 is grasped to restrain the suture material second end 504 from entering the incision 80 [FIG. 12 (b)]. The remaining steps are substantially the same as in Method Embodiment One.

Method Embodiment Three. In another embodiment, shown in FIG. 9 (a)-(c), the apparatus 10 may be inserted through a cannula or a trocar instead of being inserted directly into an incision. In this "exchange rod" technique, a trocar 90 is inserted into the incision 80 prior to the tubular body inserting step [FIG. 9 (a)]. The inserting step then further comprises inserting the tubular body 20 into the trocar 90 [FIG. 9 (b)], and removing the trocar 90 from the incision 80 [FIG. 9 (c)]. This method permits the maintenance of gas pressure within a body cavity communicating with the incision during the suturing, typically in the form of pneumoperitoneum in the case of intraperitoneal surgery.

It may be appreciated by one skilled in the art that additional embodiments may be contemplated, including other means of deploying and positioning the suture needle and other methods for using the apparatus.

In the foregoing description, certain terms have been used for brevity, clarity, and understanding, but no unnecessary limitations are to be implied therefrom beyond the requirements of the prior art, because such words are used for description purposes herein and intended to be broadly construed. Moreover, the embodiments of the apparatus illustrated and described herein by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A surgical suturing apparatus for closing an incision penetrating a plurality of layers of tissue, the apparatus comprising;

a tubular body having a longitudinal axis, an inner space, a side wall, a first end, a closed second end, and a slot through the side wall communicating with the inner space having a length generally parallel to the longitudinal axis and a width, the slot positioned generally adjacent the second end, the tubular body having an opening at the first end;

a generally "J"-shaped suture needle dimensioned to reside within the inner space of the tubular body, the suture needle having a first straight section having a proximal end and a second straight section, the first and the second straight sections each adjacent a curved middle section forming a generally "U"-shaped distal end, the distal end positioned adjacent the tubular body second end, the first straight section generally positioned along the longitudinal axis of the tubular body, the second straight section having a pointed tip and a suture gate dimensioned to allow suture material to pass therethrough, the suture gate positioned along the second straight section adjacent the pointed tip, the second straight section having a length shorter than the of the slot in the tubular body, enabling the second straight section to protrude therefrom when positioned adjacent thereto and moved in a radially outward direction;

suture needle deploying means affixed to the suture needle and movably engaged with the tubular body, the deploying means having a first end and a second end and comprising a stop means for preventing a disengagement of the deploying means and the tubular body, the deploying means movable relative to the tubular body between a deployed position wherein the suture needle second straight section is positioned to protrude from the tubular body slot, and a closed position wherein the suture needle second straight section is positioned so as to be enclosed within the inner space of the tubular body;

a first guiding means affixed to the suture needle for aiding the deploying means to move between the deployed and the closed positions; and a second guiding means affixed within the inner space of the tubular body for aligning the second straight section of the suture needle with the slot in the tubular body; and wherein:

the deploying means is affixed to the proximal end of the suture needle first straight section and has a distal portion adjacent the deploying means second end dimensioned to slide within the opening in the tubular body first end and a shoulder adjacent to and proximal of the distal portion dimensioned larger than the tubular body first end, thereby permitting the deploying means distal portion to slide into the tubular body first end until the sliding is stopped by the shoulder, wherein the closed position comprises a position wherein the shoulder is adjacent the tubular body first end;

the tubular body side wall has an inner channel adjacent the first end, the channel communicating with the inner space and having a proximal end;

the stop means comprises a protrusion adjacent the deploying means second end, the protrusion dimensioned to slide within the channel during a movement of the deploying means relative to the tubular body; and in use, when the deploying means is moved into the deployed position, the protrusion reaches the proximal end of the channel and prevents further extension of the deploying means in a proximal direction, thereby retaining the second end of the deploying means within the tubular body.

2. A surgical suturing apparatus for closing an incision penetrating a plurality of layers of tissue, the apparatus comprising:

a tubular body having a longitudinal axis, an inner space, a side wall, a first end, a closed second end, and a slot through the side wall communicating with the inner space having a length generally parallel to the longitudinal axis and a width, the slot positioned generally adjacent the second end;

a generally "J"-shaped suture needle dimensioned to reside within the inner space of the tubular body, the suture needle having a first straight section having a proximal end and a second straight section, the first and the second straight sections each adjacent a curved middle section forming a generally "U"-shaped distal end, the distal end positioned adjacent the tubular body second end, the first straight section generally positioned along the longitudinal axis of the tubular body, the second straight section having a pointed tip and a suture gate dimensioned to allow suture material to pass therethrough, the suture gate positioned along the straight section adjacent the pointed tip, the second straight section having a length shorter than the length of the slot in the tubular body, enabling the second straight section to protrude therefrom when positioned adjacent thereto and moved in a radially outward direction;

suture needle deploying means affixed to the suture needle and movably engaged with the tubular body, the deploying means movable relative to the tubular body between a deployed position wherein the suture needle second straight section is positioned to protrude from the tubular body slot, and a closed position wherein the suture needle second straight section is positioned so as to be enclosed within the inner space of the tubular body; and a first guiding means affixed to the suture needle for aiding the deploying means to move between the deployed and the closed positions, wherein the first guiding means is affixed along the curved middle section and the first straight section of the suture needle, the first guiding means having a distal end extending distalward of the suture needle curved middle section, the distal end dimensioned to remain within the tubular body inner space when the deploying means is in the deployed position, the first guiding means further having a width generally parallel to a plane formed by the first and the second straight sections of the suture needle, the width tapering downward toward the distal end, the taper aiding the movement of the deploying means in a distal direction from the deployed to the closed position by ramping the suture needle middle section into the tubular body inner space.

3. The surgical suturing apparatus recited in claim 2, wherein the first guiding means further has a proximal portion having a protrusion dimensioned and positioned, when the deploying means is in the deployed position, to plug the slot in the tubular body, thereby preventing tissue material within the incision from entering the tubular body inner space, and also preventing a loss of gas pressure from a body cavity through the apparatus.

4. The surgical suturing apparatus recited in claim 3, wherein:

the first guiding means protrusion has a ramp at the proximal end; and the tubular body side wall has a ramp adjacent a proximal end of the slot dimensioned to engage the first guiding means protrusion ramp when the deploying means is in the deployed position, thereby preventing a further movement of the suture needle in a proximal direction.

5. A surgical suturing apparatus for closing an incision penetrating a plurality of layers of tissue, the apparatus comprising:

a tubular body having a longitudinal axis, an inner space, a side wall, a first end, a closed second end, and a slot through the side wall communicating with the inner space having a length generally parallel to the longitudinal axis and a width, the slot positioned generally adjacent the second end;

a generally "J"-shaped suture needle dimensioned to reside within the inner space of the tubular body, the suture needle having a first straight section having a proximal end and a second straight section, the first and the second straight sections adjacent a curved middle section forming a generally "U"-shaped distal end positioned adjacent the tubular body second end, the first straight section generally positioned along the longitudinal axis of the tubular body, the second straight section having a pointed tip and a suture gate dimensioned to allow suture material to pass therethrough, the suture gate positioned along the second straight section adjacent the pointed tip, the second straight section having a length shorter than the length of the slot in the tubular body, enabling the second straight section to protrude therefrom when positioned adjacent thereto and moved in a radially outward direction;

suture needle deploying means affixed to the suture needle and movably engaged with the tubular body, the deploying means movable relative to the tubular body between a deployed position wherein the suture needle second straight section is positioned to protrude from the tubular body slot, and a closed position wherein the suture needle second straight section is positioned so as to be enclosed within the inner space of the tubular body, and a first guiding means affixed to the suture needle for aiding the deploying means to move between the deployed and the closed positions, wherein:

the first and the second straight sections of the suture needle are biased to flare away from a parallel orientation;

the tubular body inner space has a diameter generally normal to the longitudinal axis dimensioned to closely engage the suture needle curved middle section, so that when the suture needle curved middle section is positioned within the tubular body inner space, the suture needle first and second straight sections are prevented from flaring away from a parallel orientation;

when the deploying means is in the closed position, the suture needle curved middle section is positioned distal of the tubular body slot within the tubular body inner space, the tubular body side wall pinching the suture needle curved middle section, forcing the suture needle second straight section within the tubular body inner space; and when the deploying means is moved into the deployed position, the suture needle is moved in a proximal direction until the suture needle curved middle section and the second straight section are both positioned adjacent the tubular body slot, the suture needle curved middle section released from pinching relation with the tubular body side wall, the suture needle bias causing the suture needle second straight section to protrude from the tubular body slot.

6. The surgical suturing apparatus recited in claim 5, wherein:

the suture needle first straight section is pliable and is biased to a substantially linear orientation;

the tubular body further comprises a second guiding means affixed within the tubular body inner space for aligning the suture needle second straight section with the tubular body slot, the second guiding means comprising an element affixed along a central portion of the tubular body inner space and positioned to restrain a central portion of the suture needle first straight section generally along a central section of the tubular body side wall generally in longitudinal alignment with the tubular body slot;

when the suture needle deploying means is in the closed position, a distal end of the suture needle first straight section is restrained adjacent the tubular body side wall generally opposite the tubular body slot, bending the suture needle first straight section away from a linear orientation and away from the tubular body slot; and when the suture needle deploying means is moved to the deployed position, the suture needle first straight section bias further causes the suture needle second straight section to protrude from the tubular body slot.

7. The surgical suturing apparatus recited in claim 6, wherein the suture needle further has a bore extending from the proximal end to the suture gate, the bore dimensioned to permit suture material to pass therethrough.

8. The surgical suturing apparatus recited in claim 7, further comprising a suture lead for aiding in threading suture material through the suture needle bore, the suture lead threaded through the bore, the suture lead having a distal end protruding from the suture gate and a proximal end protruding from the suture needle first straight section proximal end, the suture lead proximal end affixable to the suture material, wherein in use the suture material is affixed to the suture lead proximal end, the suture lead distal end is pulled from the suture gate until the suture lead proximal end and suture material emerge from the suture gate.

9. The surgical suturing apparatus recited in claim 7, wherein:

the tubular body first end has an opening therein;

the deploying means has a first end and a second end;

the deploying means is engaged with the tubular body first end opening;

the deploying means has a hollow inner space and a hole through the first and the second end, each hole dimensioned to permit suture material to pass therethrough; and in use suture material is threaded through the deploying means first end hole, inner space, and second end hole, into the suture needle bore, and out the suture gate.

10. The surgical suturing apparatus recited in claim 9, further comprising tensioner means affixed within the deploying means inner space for maintaining constant tension on suture material passing through the deploying means inner space in a distal direction and for retarding movement of suture material passing in a proximal direction.

11. The surgical suturing apparatus recited in claim 10, wherein the tensioner means comprises:

a fixed element affixed within the deploying means inner space;

a pivotable element affixed within the deploying means inner space in spaced relation to the fixed element, the pivotable element movable between a locking position wherein suture material positioned between the fixed element and the pivotable element is restrained from moving and a releasing position wherein suture material passing between the fixed element and the pivotable element is generally freely movable therebetween, the pivotable element biased to the locking position.

12. The surgical suturing apparatus recited in claim 11, further comprising a stop and a torsion spring, both affixed within the deploying means inner space, and wherein:

the pivotable element comprises a pivotable pawl having a jagged curved edge generally opposite the fixed element for aiding in restraining the suture material passing between the fixed element and the pawl;

the pawl is biased to the locking position by the torsion spring;

the stop is positioned to limit the movement of the pawl caused by the torsion spring; and in use, when the suture material is pulled in the distal direction, the suture material engages the jagged curved edge of the pawl, causing the pawl to pivot, to compress the torsion spring, and to move into the releasing position, permitting the suture material to pass in the distal direction.

13. The surgical suturing apparatus recited in claim 7, wherein:

the tubular body first end has an opening therein;

the deploying means has first end and a second end;

a second end of the deploying means is engaged with the tubular body first end opening;

the deploying means has hollow inner space and a hole through the second end dimensioned to permit suture material to pass therethrough;

the deploying means further comprises means for holding a bobbin of suture material within the deploying means inner space; and in use suture material is threaded from the bobbin, through the deploying means inner space and second end hole, into the suture needle bore, and out the suture gate.

14. The surgical suturing apparatus recited in claim 13, wherein the deploying means second end has a distal portion dimensioned to slide within the tubular body first end and a shoulder adjacent to and proximal of the distal portion dimensioned larger than the tubular body first end opening, thereby permitting the deploying means distal portion to slide into the tubular body first end until the sliding is stopped by the shoulder, wherein the closed position comprises a position wherein the shoulder is adjacent the tubular body first end.

15. The surgical suturing apparatus recited in claim 6, further comprising a sealing gasket affixed within the tubular body inner space in sealing relation to the tubular body side wall and to the second guiding means, the sealing gasket having a hole therein dimensioned to closely engage the suture needle first straight section for preventing a passage of gas through the apparatus between the tubular body slot and the tubular body first end.

16. A surgical suturing apparatus for closing an incision penetrating a plurality of layers of tissue, the apparatus comprising:

a tubular body having a longitudinal axis, an inner space, a side wall, a first end, a closed second end, and a slot through the side wall communicating with the inner space having a length generally parallel to the longitudinal axis and a width, the slot positioned generally adjacent the second end;

a generally "J"-shaped suture needle dimensioned to reside within the inner space of the tubular body, the suture needle having a first straight section having a proximal end and a second straight section, the first and the second straight sections each adjacent a curved middle section forming a generally "U"-shaped distal end, the distal end adjacent the tubular body second end, the first straight section generally positioned along the longitudinal axis of the tubular body, the second straight section having a pointed tip and a suture gate dimensioned to allow suture material to pass therethrough, the suture gate positioned along the second straight section adjacent the pointed tip, the second straight section having a length shorter than the length of the slot in the tubular body, enabling the second straight section to protrude therefrom when positioned adjacent thereto and moved in a radially outward direction; and suture needle deploying means affixed to the suture needle and movably engaged with the tubular body, the deploying means movable relative to the tubular body between a deployed position wherein the suture needle second straight section is positioned to protrude from the tubular body slot, and a closed position wherein the suture needle second straight section is positioned so as to be enclosed within the inner space of the tubular body, wherein:

the deploying means comprises:

a deploying member affixed to the suture needle and having an operating portion exterior to the tubular body; and a camming member affixed at least partially within the tubular body inner space to the suture needle and having a radially extending protrusion; and the tubular body further comprises a camming slot communicating with the tubular body inner space dimensioned and adapted to slidably engage the first camming member protrusion, the camming slot having a first end and a second end, the camming member and camming slot positioned so that, when the camming member protrusion is positioned at the camming slot first end, the suture needle second straight section is enclosed within the tubular body inner space, and so that, when the camming member protrusion is positioned at the camming slot second end, the suture needle second straight section is deployable through the tubular body slot and outside the tubular body side wall.

17. The surgical suturing apparatus recited in claim 16, wherein:

the tubular body has an open first end; and the deploying member is affixed to the proximal end of the suture needle first straight section and has a distal portion dimensioned to slide within the tubular body first end and a shoulder adjacent to and proximal of the distal portion dimensioned larger than the tubular body first end, thereby permitting the deploying means distal portion to slide into the tubular body first end until the sliding is stopped by the shoulder, wherein the closed position comprises a position wherein the shoulder is adjacent the tubular body first end.

18. The surgical suturing apparatus recited in claim 17, wherein:

the camming member is affixed adjacent the suture needle distal end; and the camming slot is positioned adjacent the tubular body second end.

19. The surgical suturing apparatus recited in claim 16, wherein:

the first and the second straight sections of the suture needle are biased to flare away from a parallel orientation; and when the deploying means is moved into the deployed position, wherein the suture needle second straight section is positioned adjacent the tubular body slot, the suture needle bias causes the suture needle second straight section to protrude therefrom.

20. A surgical suturing apparatus for closing an incision penetrating a plurality of layers of tissue, the apparatus comprising:

a tubular body having a longitudinal axis, an inner space, a side wall, a first end, a closed second end, and a slot through the side wall communicating with the inner space having a length generally parallel to the longitudinal axis and a width, the slot positioned generally adjacent the second end;

a generally "J"-shaped suture needle dimensioned to reside within the inner space of the tubular body, the suture needle having a first straight section having a proximal end and a second straight section, the first and the second straight sections each adjacent a curved middle section forming a generally "U"-shaped distal end, the distal end positioned adjacent the tubular body second end, the first straight section generally positioned along the longitudinal axis of the tubular body, the second straight section having a pointed tip and a suture gate dimensioned to allow suture material to pass therethrough, the suture gate positioned along the second straight section adjacent the pointed tip, the second straight section having a length shorter than the length of the slot in the tubular body, enabling the second straight section to protrude therefrom when positioned adjacent thereto and moved in a radially outward direction; and suture needle deploying means affixed to the suture needle and movably engaged with the tubular body, the deploying means movable relative to the tubular body between a deployed position wherein the suture needle second straight section is positioned to protrude from the tubular body slot, and a closed position wherein the suture needle second straight section is positioned so as to be enclosed within the inner space of the tubular body, wherein:

the first and the second straight sections of the suture needle are biased to flare away from a parallel orientation;

a distal portion of the first straight section of the suture needle is biased to curve in a direction toward the second straight section, so that, when the deploying means is moved into the deployed position, wherein the suture needle second straight section is positioned adjacent the tubular body slot, the suture needle biases cause the second straight section to protrude therefrom;

a central portion of the first straight section of the suture needle has a ramp therein, a top part of the ramp extending in a direction generally toward the tubular body side wall adjacent the tubular body slot; and the deploying means comprises longitudinally slidable covering means having:

a proximal section comprising means exterior to the tubular body for effecting a sliding of the covering member relative to the tubular body; and a central section extending generally along an inner wall of the tubular body inner space proximal of and generally longitudinally aligned with the tubular body slot, the central section having a protrusion adapted to be adjacent to and distal of the suture needle ramp when the deploying means is in the deployed position and to be proximal of the suture needle ramp when the deploying means is in the closed position, a cooperative action between the suture needle ramp and the protrusion when moving the deploying means from the deployed to the closed position serving to push the suture needle first straight section toward the tubular body inner wall radially opposite the tubular body slot, thereby moving the suture needle distal end within the tubular body inner space;

a distal section comprising means covering a portion of the tubular body slot and slidable relative thereto, the distal section adapted to be positioned at a bottom of the slot when the deploying means is in the deployed position, permitting the suture needle first and second straight sections to flare away from each other, and to be positioned at a top of the slot when the deploying means is in the closed position; covering the suture needle pointed tip and preventing the suture needle first and the second straight sections from flaring.

21. The surgical suturing apparatus recited in claim 20, wherein the covering means central section further has a brace proximal of the protrusion extending radially across the tubular body inner space to restrain a central portion of the suture needle first straight section against the tubular body inner wall radially opposite and proximal of the tubular body slot, thereby restraining the bias in the distal portion of the suture needle first straight section at a point of contact therebetween.

22. A method for suturing an incision penetrating a plurality of layers of tissue, the me hod comprising the steps of:

providing a surgical suturing apparatus comprising:

a tubular body having a longitudinal axis, an inner space, a side wall, a first end, a closed second end, and a slot through the side wall communicating with the inner space having a top, a length generally parallel to the longitudinal axis, and a width, the slot positioned adjacent the second end;

a generally "J"-shaped suture needle dimensioned to reside within the inner space of the tubular body, the suture needle further having a first straight section having a proximal end and a second straight section, the first and the second straight sections each adjacent a curved middle section forming a generally "E"-shaped distal end, the distal end positioned adjacent the tubular body second end, the first straight section generally parallel to the longitudinal axis of the tubular body, the second straight section having a pointed tip and a suture gate dimensioned to allow suture material to pass therethrough, the suture gate positioned along the second straight section adjacent the pointed tip, the second straight section having a length shorter than the length of the slot in the tubular body, enabling the second straight section to protrude therefrom when positioned adjacent thereto and moved in a radially outward direction; and suture needle deploying means affixed to the suture needle and movably engaged with the tubular body, the deploying means movable relative to the tubular body between a deployed position wherein the suture needle second straight section is positioned to protrude from the tubular body slot, and a closed position wherein the suture needle second straight section is positioned so as to be enclosed within the inner space of the tubular body;

providing suture material threaded through the suture gate the suture material having a first end emerging from the suture gate and a second end;

moving the deploying means into the closed position;

inserting the tubular body of the surgical suturing apparatus into the incision, the second end of the tubular body inserted first, sufficiently far that the top of the slot is positioned beneath the deepest tissue layer to be sutured;

deploying the suture needle into the deployed position, the pointed tip thereby protruding from the tubular body beneath the deepest tissue layer to be sutured;

positioning the pointed tip in a first suturing position;

bringing the tubular body n a direction out of the incision sufficiently far that the pointed tip pierces the tissue layer to be sutured and extends thereabove;

grasping the first end of the suture material;

pulling the first end of the suture material out of the incision;

pushing the tubular body in a direction into the incision sufficiently far that the pointed tip is positioned beneath the tissue layer to be sutured;

rotating the tubular body to position the pointed tip in a second suturing position;

bringing the tubular body in a direction out of the incision sufficiently far that the pointed tip pierces the tissue layer to be sutured and extends thereabove;

grasping the suture material at a location where the suture material is emerging from the suture gate;

pulling the suture material out of the incision at the location grasped;

bringing the tubular body out of the incision; and tying a knot in the suture material, thereby closing the incision in the tissue layer.

23. The suturing method recited in claim 22, further comprising the step, preceding the tubular body inserting step, of inserting a trocar into the incision, and wherein the inserting step further comprises inserting the tubular body into the trocar, and further comprising the step, following the tubular body inserting step, of removing the trocar from the incision, thereby maintaining gas pressure within a body cavity communicating with the incision during the suturing.

24. The suturing method recited in claim 22, wherein:

the suture needle has a bore therethrough extending from a proximal end of the suture needle first straight section to the suture gate; and the suture material providing step comprises threading suture material through the bore.

25. A method for suturing an incision penetrating a plurality of layers of tissue, the method comprising the steps of:

providing a surgical suturing apparatus comprising:

a tubular body having a longitudinal axis, an inner space, a side wall, a first end, a closed second end, and a slot through the side wall communicating with the inner space having a top, a length generally parallel to the longitudinal axis, and a width, the slot positioned adjacent the second end;

a generally "J"- shaped suture needle dimensioned to reside within the inner space of the tubular body, the suture needle further having a first straight section having a proximal end and a second straight section, the first and the second straight sections each adjacent a curved middle section forming a generally "U"-shaped distal end, the distal end positioned adjacent the tubular body second end, the first straight section generally parallel to the longitudinal axis of the tubular body, the second straight section having a pointed tip and a suture gate dimensioned to allow suture material to pass therethrough, the suture gate positioned along the second straight section adjacent the pointed tip, the second straight section having a length shorter than the length of the slot in the tubular body, enabling the second straight section to protrude therefrom when positioned adjacent thereto and moved in a radially outward direction; and suture needle deploying means affixed to the suture needle and movably engaged with the tubular body, the deploying means movable relative to the tubular body between a deployed position wherein the suture needle second straight section is positioned to protrude from the tubular body slot, and a closed position wherein the suture needle second straight section is positioned so as to be enclosed within the inner space of the tubular body;

moving the deploying means into the closed position;

inserting the tubular body of the surgical suturing apparatus into the incision, the second end of the tubular body inserted first, sufficiently far that the top of the slot is positioned beneath the deepest tissue layer to be sutured;

deploying the suture needle into the deployed position the pointed tip thereby protruding from the tubular body beneath the deepest tissue layer to be sutured;

positioning the pointed tip in a first suturing position;

bringing the tubular body in a direction out of the incision sufficientyl far that the pointed tip pierces the tissue layer to be sutured and extends thereabove;

bringing the tubular body further out of the incision to expose the pointed tip above a cutaneous layer, avoiding piercing the cutaneous layer with the pointed tip;

threading a first end of suture material through the suture gate;

grasping a second end of the suture material to restrain the suture material second end from entering the incision;

pushing the tubular body in a direction into the incision sufficiently far that the pointed tip is positioned beneath the tissue layer to be sutured;

rotating the tubular body to position the pointed tip in a second suturing position;

bringing the tubular body in a direction out of the incision sufficiently far that the pointed tip pierces the tissue layer to be sutured and extends thereabove;

grasping the suture material at the first end;

pulling the suture material out of the incision at the location grasped;

bringing the tubular body out of the incision; and tying a knot in the suture material, thereby closing the incision in the tissue layer.

* * * * *